US010776516B2

(12) United States Patent
Dinov et al.

(10) Patent No.: US 10,776,516 B2
(45) Date of Patent: Sep. 15, 2020

(54) ELECTRONIC MEDICAL RECORD DATASIFTER

(71) Applicant: The Regents of The University of Michigan, Ann Arbor, MI (US)

(72) Inventors: Ivaylo Dinov, Ann Arbor, MI (US); John Vandervest, Ann Arbor, MI (US); Simeone Marino, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 227 days.

(21) Appl. No.: 16/051,881

(22) Filed: Aug. 1, 2018

(65) Prior Publication Data

US 2019/0042791 A1     Feb. 7, 2019

Related U.S. Application Data (60) Provisional application No. 62/540,184, filed on Aug. 2, 2017.

(51) Int. Cl.
| | | |
|---|---|---|
| G06F 16/00 | (2019.01) | |
| G06F 21/62 | (2013.01) | |
| G16H 10/60 | (2018.01) | |
| G06N 7/08 | (2006.01) | |
| G06F 17/18 | (2006.01) | |
| G06F 17/11 | (2006.01) | |
| G16H 50/70 | (2018.01) | |

(Continued)

(52) U.S. Cl.
CPC ...... *G06F 21/6254* (2013.01); *G06F 16/2272* (2019.01); *G06F 17/11* (2013.01);
(Continued)

(58) Field of Classification Search
None
See application file for complete search history.

(56) References Cited

U.S. PATENT DOCUMENTS

| | | |
|---|---|---|
| 7,653,615 B2 | 1/2010 | Dwork et al. |
| 7,698,250 B2 | 4/2010 | Dwork et al. |

(Continued)

OTHER PUBLICATIONS

X. Yao et al "Differential Privacy of Big Data: An Overview" Big Data Security on Cloud (BigDataSecurity), IEEE International Conference on High Performance and Smart Computing (HPSC) and IEEE International Conference on Intelligent Data and Security (2016).

(Continued)

*Primary Examiner* — Bai D Vu
(74) *Attorney, Agent, or Firm* — Harness, Dickey & Pierce, P.L.C.

(57) ABSTRACT

A method is presented for generating a data set from a database. The method involves iterative data manipulation that stochastically identifies candidate entries from the cases (subjects, participants) and variables (data elements) and subsequently selects, nullifies, and imputes the information. This process heavily relies on statistical multivariate imputation to preserve the joint distributions of the complex structured data archive. At each step, the algorithm generates a complete dataset that in aggregate closely resembles the intrinsic characteristics of the original data set, however, on an individual level the rows of data are substantially altered. This procedure drastically reduces the risk for subject reidentification by stratification, as meta-data for all subjects is repeatedly and lossily encoded.

19 Claims, 3 Drawing Sheets

(51) Int. Cl.
*G06F 16/22* (2019.01)
*G06N 5/00* (2006.01)
*G06N 7/00* (2006.01)
*G06N 20/20* (2019.01)

(52) U.S. Cl.
CPC .............. *G06F 17/18* (2013.01); *G06N 7/08* (2013.01); *G16H 10/60* (2018.01); *G16H 50/70* (2018.01); *G06N 5/003* (2013.01); *G06N 7/005* (2013.01); *G06N 20/20* (2019.01)

(56) References Cited

U.S. PATENT DOCUMENTS

| 8,140,502 B2 | 3/2012 | Francis et al. |
| 2014/0283091 A1 | 9/2014 | Zhang et al. |
| 2017/0091391 A1* | 3/2017 | LePendu ............... G06F 40/279 |

OTHER PUBLICATIONS

G. Nelson "Practical Implications of Sharing Data: A Primer on Data Privacy Anonymization and De-Identification", www.researchgate.net/publication/318866074 (Apr. 2015).

C. Dwork, "Differential Privacy: A Survey of Results", International Conference on Theory and Applications of Models of Computation. Springer Berlin Heidelberg (2008).

R. Rogers et al "Max-Information, Differential Privacy, and Post-Selection Hypothesis Testing", 2016 IEEE 57th Annual Symposium on Founcations of Computer Science (FOCS) (2016).

C. Dwork et al "The Reusable Holdout: Preserving Validity in Adaptive Data Analysis", Science 349.6248 (2015).

* cited by examiner

FIG. 4

ELECTRONIC MEDICAL RECORD DATASIFTER

CROSS-REFERENCE TO RELATED APPLICATIONS

This application claims the benefit of U.S. Provisional Application No. 62/540,184, filed on Aug. 2, 2017. The entire disclosure of the above application is incorporated herein by reference.

GOVERNMENT CLAUSE

This invention was made with government support under Grant No. NR015331 awarded by the National Institutes of Health and Grant No. IIS-1636840 awarded by the National Science Foundation. The government has certain rights in the invention.

FIELD

The present disclosure relates to a system and method for sharing clinical data and other types of data without compromising the identity of individuals or entities to whom the data pertains.

BACKGROUND

Currently, there are no practical, scientifically reliable, and effective mechanisms to share real clinical data without compromising the data, or the identity of individuals, or other sensitive personal information to whom the data pertains. Cohort stratification approaches looking at large data archives may be misused by various actors aiming for re-identification of specific cases. To advance scientific understanding of the human conditions, the usefulness of releasing sifted de-identified data for research purposes trades off with the potential risk to re-identify individuals by narrowly stratifying sub cohorts in the entire data archive based on repeated mapping of known features for the specific case. Thus, an improved method is needed for creating data sets without compromising the identity of individuals or entities to whom the data pertains This section provides background information related to the present disclosure which is not necessarily prior art.

SUMMARY

This section provides a general summary of the disclosure, and is not a comprehensive disclosure of its full scope or all of its features.

A computer-implemented method is presented for generating a data set from a database. The method includes: receiving a set of records from a database, each record pertains to a particular entity and is comprised of a plurality of data fields; identifying data fields in the set of records that contain explicitly identifiable data for an entity; obfuscating values in the data fields identified as containing explicitly identifiable data for the entity; removing values in randomly selected data fields of randomly selected records in the set of records; imputing values in data fields having missing values in the set of records using an imputation method; and repeating the steps of removing values and imputing values for a number of iterations and thereby generate a new data set.

Values in the data fields identified as containing explicitly identifiable data may be obfuscated by removing the values from the identified data fields.

Values in randomly selected data fields may be removed by randomly selecting data fields in the set of records using an alias method.

Values in data fields may be imputed using multivariate imputation by chained equations.

Prior to the step of removing values in the data fields, the method may further include: identifying data fields in the set of records having unstructured data format and swapping values of at least one identified data field in a given pair of data records, where the given pair of data records is selected using a similarity measure between the data records in the set of records.

In one embodiment, the given pair of data records is selected by pairing a given data record in the set of records with each of the other data records in the set of records; computing a similarity measure between values of data fields in each pair of records; and identifying the given pair of records from amongst the pair of records, where the given pair of records has the highest similarity measure amongst the pair of records.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
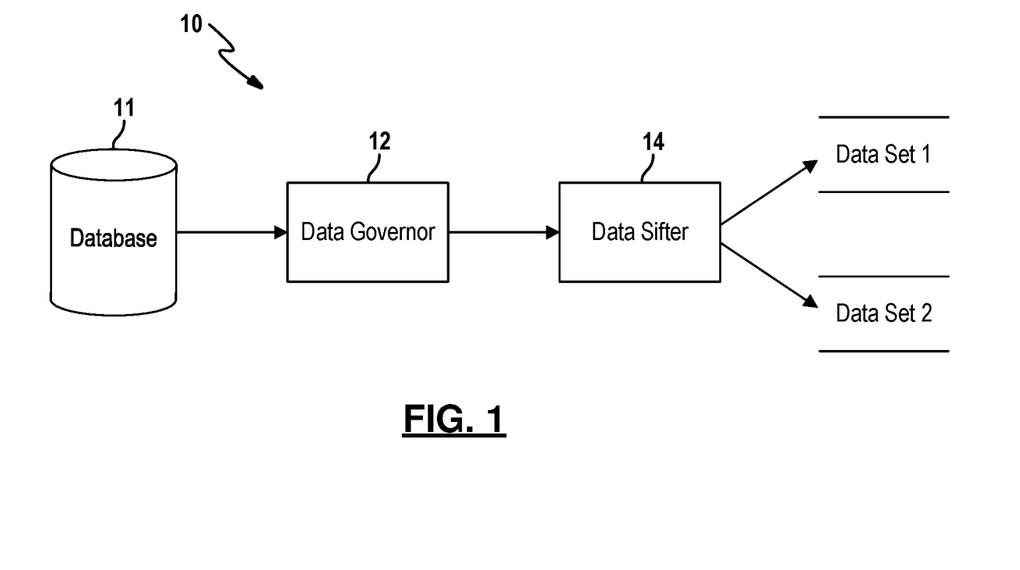
FIG. 1 is a block diagram of a system for sharing data in accordance with this disclosure.

FIG. 1 depicts a system 10 for sharing data without compromising the identity of individuals or entities to whom the data pertains. The system 10 is comprised of a data governor 12, a data sifter 14 and a database 11. In one embodiment, the database 11 hosts electronic medical records for numerous persons. Researchers and non-clinical investigators may have an interest in accessing and using the data for various purposes including scientific modeling and research, exploratory and confirmatory analytics, etc. While reference is made throughout this disclosure to medical records, the system 10 has application to other types of data including sensitive information, such as census data, data from the IRS, finance and investment information.

In operation, the data governor 12 receives requests for data from a requestor and extracts raw data that meets the request from the database 11. For illustration purposes, the data request may be "I need all cases (patients and controls) from the database (e.g., EMR/Epic) that meet these criteria: 55<age<75; have an MRI brain scan in the past 24 months; have a clinical assessment (e.g., physician notes); with race distribution Whites:Others is 1:1; 3.9 mmol/L<glucose level<5.5 mmol/L; 25<MMSE<30". The data governor 12 translates this qualitative data request into a SQL query for the database. In this example, the SQL query is as follows.

SELECT *
FROM UMHS-EPIC
WHERE Age>=55 AND Age<=75 AND
Brain_MRI_Scan_Indicator='Yes' . . .
ORDER BY MRN;

which returns the records (e.g., medical record numbers) of all subjects/cases in the database that meet these criteria. An SQL query is merely illustrative and it is understood that the type of query may vary with the type of database. The data governor 12 extracts an instance of the (raw) data and exports it to a raw data object. Particular methods for translating a data request into a database query are known and are not further described in this disclosure.

In an example embodiment, the data request includes a level of obfuscation (η) that needs to be applied before the raw data is given to the requestor. The level of obfuscation may be specified by the data governor as a value between zero and one, where zero indicates that the raw data is given to the requestor and one indicates that entirely synthetic data is given to the requestor. In other instances, the level of obfuscation may be assigned by the data governor depending on the identity of the requestor. For example, the level of obfuscation is set at or near zero for a trusted requestor while most requestors are assigned larger values (e.g., exceeding 0.5).

When the level of obfuscation exceeds a minimal value (e.g., 0.2), the data governor 12 will obfuscate values in select data fields that contain explicitly identifiable data for a person or an entity to which the data pertains. For example, data fields which contain the name, address, birth date, social security number and/or medical record number for a person may be selected and explicitly removed. In another example, the data may be tax records for a person, a corporation or a non-profit entity. Likewise, data fields which contain name, address, tax identification number and/or other identifiable data may be selected and obfuscated by the data governor. The data governor 12 typically implement predefined rule set for selecting the data fields to be explicitly removed and/or obfuscated in accordance with organizational policies, local, state and/or federal regulations. The values in the selected data field can then be obfuscated by replacing the values in the data field with synthetic values, assigning randomized unique substitutes to the values, or by completely removing the values from the selected data fields. The particular data fields identified above are merely intended to be illustrative and are not limiting. It is also envisioned that obfuscating values in data fields that contain explicitly identifiable data may be implemented by the data sifter 14 instead of the data governor 12.

Upon receipt of the data from the data governor 12, the data sifter 14 uses an algorithm that involves iterative data manipulation that stochastically identifies candidate data fields in the records and subsequently selects, nullifies and imputes the information contained in the records. This process relies on statistical multivariate imputation to preserve the joint distributions of the complex structured data. At each step, the algorithm generates a complete dataset that in aggregate closely resembles the intrinsic characteristics of the original cohort while on an individual level the rows of data are substantially altered. This approach drastically reduces the risk for subject re-identification by stratification as metadata for all subjects is repeatedly and lossily encoded. The steps for an example algorithm are further described below.

Figure 2:
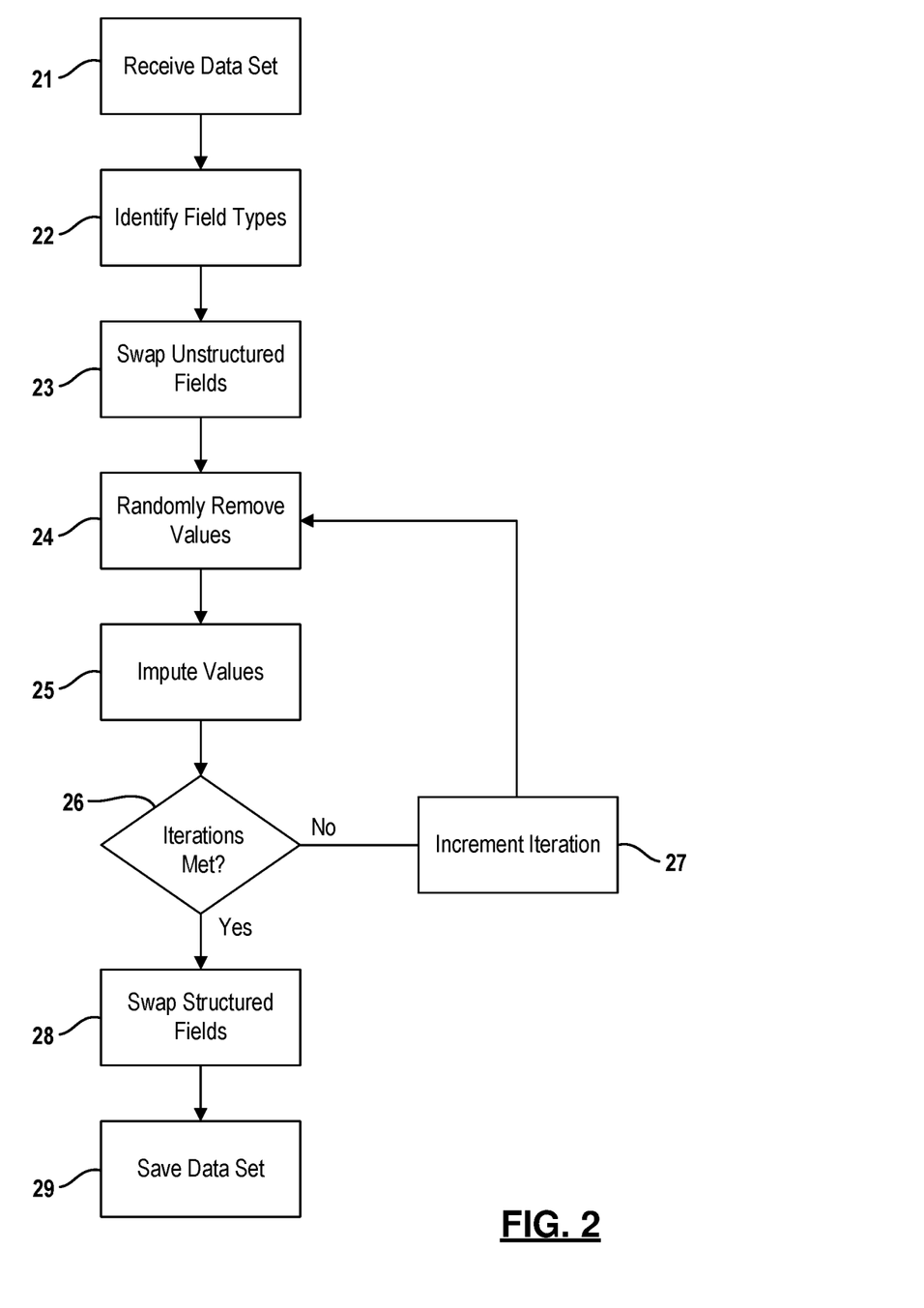
FIG. 2 is a flowchart depicting an overview of the data sifter.

FIG. 2 provides an overview of the steps performed by the data sifter 14. As a starting point, the data sifter 14 receives a set of records extracted from the database 11 as indicated at 21. In the example embodiment, the set of records are received from the data governor 12. Each record is comprised of a plurality of data fields and pertains to a particular person or entity (e.g. company).

For each data field, the type of data field is identified at 22. For example, a data field may be tagged as a DATE field if it contains a date. One technique for classifying a field as a DATE is any data field whose name includes the case independent string "date". In another example, a data field may be classified as a structured field or an unstructured field, where an unstructured field may be a comment field or a note from a healthcare provider. In yet another example, a data field may be classified as having values that fall within categories, such as gender or race of a person, type of an organization or business, or states of a country. Structured and unstructured features can be discriminated by computing the number of unique values, across all records, for the specific data field. As an example, if there are one million records, and there are less than 3*log(1,000,000)=3*6=18 unique values across all records, the features will be considered categorical. If the number of unique values exceeds 18, then the feature may be considered as numerical. Similar rules may be applied to automate the classification and labeling of features as discrete, ordinal, or non-ordinal. The distribution of the lengths of the values stored across records within a specific feature also helps determine unstructured data fields. For instance, clinical notes, text, audio, images, video, timeseries, etc. can easily be separated from other structured features. Unstructured fields typically contain strings over 128 character long that either represent the raw data (e.g., human readable text) or meta-data (pointers or references to the actual data, which may be stored as non-human readable text of machine language code). It is understood that a data field may be tagged with more than one classification. In the example embodiment, type identifiers for each of the data fields are received by the data sifter 14 as an input from the data governor 12. In other embodiments, the classifying of the data fields by type may be automatically performed by the data sifter 14.

Data fields having unstructured data are obfuscated first as indicated at 23. More specifically, data fields having an unstructured data format are identified and values in those fields are swapped with each other. One example embodiment for implementing this swapping feature is further described below in relation to FIG. 3. Other techniques for identifying and swapping values in data fields with unstructured formats are also contemplated by this disclosure.

Next, the data fields in the data records are obfuscated further with an iterative process. At step 24, values of randomly selected data fields in randomly selected records are removed. In one embodiment, the selected data fields and the selected records are chosen randomly using an alias method. For example, the missForest algorithm may be used to randomly select records and/or randomly select data fields in the records. In particular, the data sifter 14 uses missForest::prodNA( ) which relies on sample( ) and the Walker's alias method. Further details regarding the missForest algorithm may be found in an article by Daniel J. Stekhoven and Peter Buhlmann entitled "MissForest—non-parametric missing value imputation for mixed-type data", Bioinformatics, Vol. 28 no 1 2012 which is incorporated by reference in its entirety.

Additionally, seeding may be introduced for additional control of the selection of the data records and/or data fields. Many other random number generation methods can also be used to produce the indices for selecting either the records and/or the data fields in the records. Examples of other random number generators that can produce the desired random indices, based on the presence or absence (default) of a seed, include but are not limited to "Mersenne-Twister", "Wichmann-Hill" (period $7 \times 10^{12}$), "Marsaglia-Multicarry" (period$>10^{18}$), "Super-Duper" (period of about $>4 \times 10^{18}$), "Mersenne-Twister", "Knuth-TAOCP-2002", which uses lagged Fibonacci sequences with subtraction and has period$>10^{36}$, and "L'Ecuyer-CMRG" (period$>10^{56}$).

Next, values in data fields having missing values in the set of records are imputed at step 25. In one embodiment, the data values are completed iteratively and jointly using multivariate imputation. The results of this approach typically generate a number of complete data chains which may be either used as is or aggregated into a single complete dataset. For mixed-type data, one such example imputation method is based on the 'missForest' package (DOI: 10.1093/bioinformatics/btr597), which allows complex interactions and nonlinear relations and generates out-of-bag imputation error estimates.

Other example imputation methods include but are not limited to chained equations, Gibbs sampling, Predictive mean matching, Bayesian linear regression, Linear regression by ignoring model error, bootstrap, or predicted values, Unconditional mean imputation, Two-level normal imputation, Imputation at level-2 of the class mean, Bayesian linear regression, or Predictive mean matching, Imputation of quadratic terms, Logistic regression, logistic regression with bootstrap, or Polytomous logistic regression, Proportional odds model, Linear discriminant analysis, Classification and regression trees, Random forest imputations, Fast predictive mean matching, etc. It is understood that the values in the imputed data fields may have been removed artificially in the previous step or were missing in the raw data received by the data sifter 14.

The steps of removing values and imputing values are repeated for a number of iterations as indicated at step 26, where the number of iterations exceeds one. The number of iterations may be a fixed number that is a user defined input as will be further described below. In some cases, the number of iterations may vary until the resulting data set meets a convergence criterion. Examples of convergence criteria include, but are not limited to: the magnitude of the difference between the completed data instances obtained in consecutive neighboring iteration runs is less than a certain threshold (first order criterion); the variability between the reconstructed instances of complete datasets at consecutive iterations is below certain threshold level (second order criterion); or a higher order criteria (e.g., based on skewness, kurtosis, various distance measures) are also possible. Each iteration results in an obfuscated data set which may serve as an output. After the iterative process is completed, the final data set is saved off in a non-transitory memory as indicated at step 29. The final data set can then be provided by the data sifter 14 to the data requester.

In some embodiments, the data sifter 14 may perform an additional swapping step at 28 before saving off the final data set. In this case, data fields other than those having an unstructured data format are considered for swapping. The extent of data fields being swapped may be controlled by one or more user-defined parameters. Again, an example embodiment for implementing this swapping feature is further described below in relation to FIG. 3 although other techniques also fall within the scope of this disclosure. It is to be understood that only the relevant steps of the methodology are discussed in relation to FIG. 2, but that other software-implemented instructions may be needed to control and manage the overall operation of the system.

In the example embodiment, the level of obfuscation performed by the data sifter 14 is controlled by one or more parameters. Five example parameters are described below. k0 determines whether or not to obfuscate data fields with an unstructured data format. Most commonly, k0 is a binary option where 1 indicates that the data fields with an unstructured data format are obfuscated and 0 indicates that the data fields with unstructured data format are not obfuscated (i.e., step 23 in FIG. 2 is skipped); however k0 may also be specified through a probability mass or a probability density function. k1 sets a percentage of data fields in a data set which have their values remove and imputed, for example in steps 24 and 25 of FIG. 2. By way of example, k1 may have a value from 0 to 40%. For each data record, this parameter indicates the relative proportion of data fields that will be randomly selected, labeled for deletion, removed and later re-imputed. Larger and smaller k1 values correspond to more or less severe obfuscation, respectively. For instance, setting k1=0.2 corresponds to 20% of the data fields being artificially obfuscated. In the example embodiment, the k1 value is an input parameter to the missForest algorithm. This will automatically wipe out one out of five data field values, e.g., missForest::prodNA(myDataset, noNA=k1=0.2). In this way, the rate at which missing values are introduced may be controlled by a user-defined parameter, k1.

For deeper obfuscation, one can also repeat this process multiple times. k2 is an integer that sets the number of iterations for removing and imputing values in steps 24 and 25. k3 sets a percentage of data fields with a structured data format that are to be obfuscated, for example in step 28. For instance, the k3 may be a percentage between zero and 100% that will apply to all of the features (or data fields) in the data set. Lastly, k4 defines a similarity measure between records that are to be swapped, where values of the data fields are swapped with corresponding data fields in records meeting the similarity measure. Additional types of parameters may be defined for controlling the level of obfuscation and thus fall within the scope of this disclosure.

Figure 3:
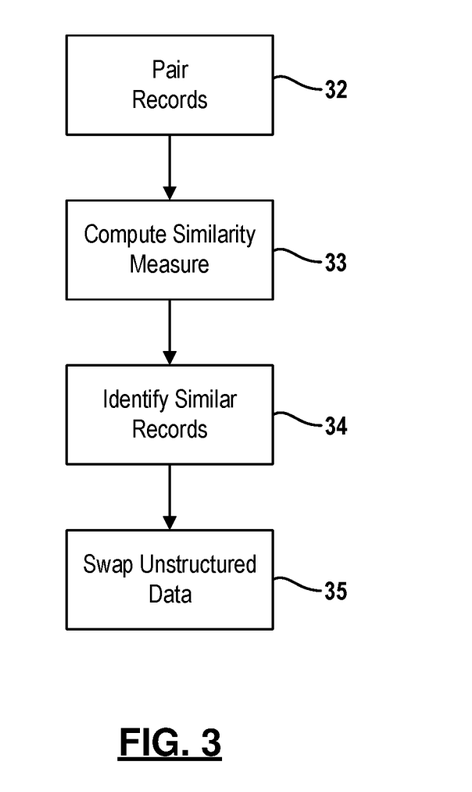
FIG. 3 is a flowchart depicting an example technique for obfuscating data by swapping values of data fields.

FIG. 3 depicts one example technique for obfuscating data by swapping values of the data fields amongst different data records. Data records are first paired with each other in step 32. In particular, a given record in a data set is paired with each of the other records in the data set. This pairing process is then repeated for each record in the data set.

Next, a similarity measure is computed at 33 for each pair of records. In one embodiment, the similarity measures are distances between data records computed using a Bray-Curtis distance method which is stable and generates few singularities. These distances are used to determine spheres-of-influence, or neighborhoods, of records that are generally similar. A distance matrix is computed that represents the "similarity" between any two cases in the entire data set. For instance, the R ecodist:distance( ) function provides an extensible, efficient and scalable approach for completing the diagonal similarity matrix that captures the relative distances from each data record. Numerical, factorial, categorical and string/unstructured features may be used when determining neighborhoods containing the closest, most similar records to a given record (which represents the center of its own neighborhood). Other alternative distance metrics include but are not limited to "Euclidean", "Bray-Curtis", "Manhattan", "Mahalanobis", "Jaccard", "Difference", "Sorensen", "Gower", "Modified Gower base b (e.g., 2, 10)", etc. More general metrics can also be used, for example, total variation, $L_p$. The similarity distance matrix is effectively a lower-triangular distance matrix as an object of class "dist" containing 0.5*N(N−1) measures representing the paired distances between each pair of cases, where N=total number of cases. In this way, the similarity distance matrix is used to identify alike cases, for example whose unstructured data elements (e.g., clinical notes) can be swapped at step 23. Similarity-based swapping of data gives an additional level of obfuscation and may also be applied to structured data elements, for example in optional step 28.

Returning to FIG. 3, records having a high degree of similarity are identified at 34 using the computed similarity measure. In one simple embodiment, data fields are swapped in the pair of records having the highest degree of similarity. Likewise, data fields may be swapped in a subset of record pairs (e.g., a predefined percentage of record pairs). Alternatively, data fields may be swapped in each of the data records as will be further described in relation to FIG. 4. In any case, values in one or more data fields in the identified record pairs are swapped at 35 and thereby introduce another level of obfuscation that significantly inhibits the probability of stratification-based re-identification of the cases, without compromising the univariate feature distributions. One can also model higher-order associations, e.g., bivariate correlations, and do a similar sifting obfuscation preserving the bivariate, and higher-order, joint feature distributions.

Figure 4:
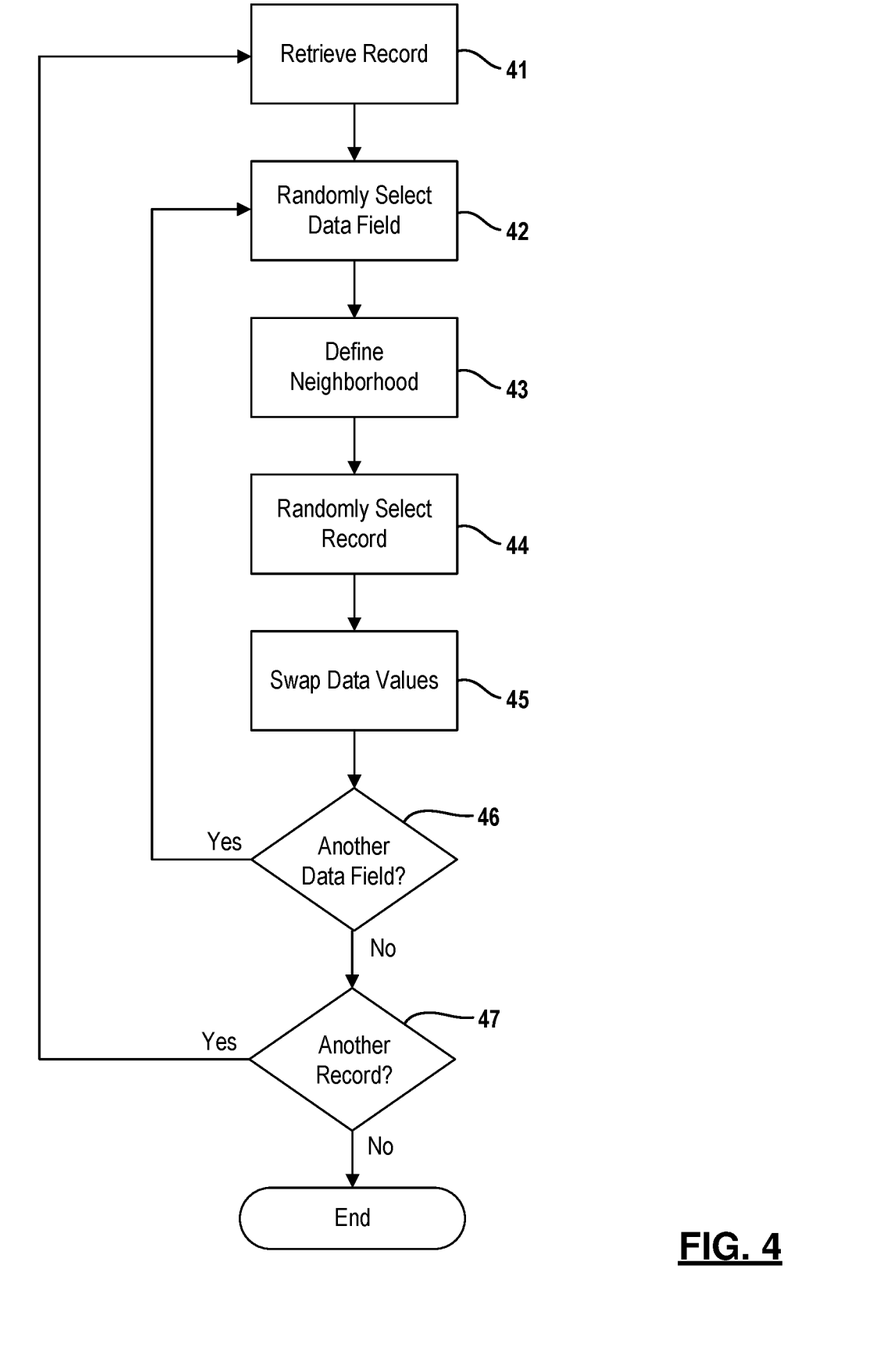
FIG. 4 is a flowchart depicting an example technique for swapping data field values amongst each of the data records in a data set.

FIG. 4 depicts one example technique for swapping data field values in amongst each of the data records. For a given data set, each record is retrieved individually at step 41. In the example embodiment, k3 sets the percentage of data fields in a given data record that are to be swapped. For illustration purposes, when k3 is set to 30% and the given data record contains 10 data fields, values will be swapped in three of the ten data fields. In the case of step 23 in FIG. 2, this means values will be swapped in three of ten data fields having an unstructured field type. In the case of step 28 in FIG. 2, this means values will be swapped in 30% of the data fields excluding the data fields having an unstructured field type (e.g., 6 of 20 structured data fields).

For a given data record, a data field in the given data record is randomly selected as indicated at 42. The data field may be selected using one of many known method, such as an alias method. In the example embodiment, k4 defines neighborhood at 43. In particular, k4 defines the percentile of the closest neighbors to the given data record from which to select a record. For illustration purposes, when k4 is set to 25% and the total number of data records is 100, the neighborhood is comprised of the twenty-five data records with the highest similarity (i.e., smallest distance measure) to the given record. From amongst the data records comprising the neighborhood, one record is randomly selected as indicated at 44. Again, the data record may be selected using one of many known methods, such as an alias method. Other techniques for randomly selecting a data field and/or a data record also fall within the scope of this disclosure.

The value is the selected data field of the given record is then swapped at 45 with the value in the corresponding data field on the randomly selected neighbor. When more than one data field is to be swapped the given data record, the process is repeated as indicated at step 46. The processes is repeated until the specified percentage of data fields has been achieved; that is three in example set forth above. After the swapping process has been completed for the given record, the process is repeated for the next record as indicated at step 47. This process is again repeated for each record in the data set. It is to be understood that only the relevant steps of the methodology are discussed in relation to FIG. 4, but that other software-implemented instructions may be needed to control and manage the overall operation of the system.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, optical storage, and Cloud storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A computer-implemented method for generating a data set from a database, comprising:
    receiving a set of records from a database, each record pertains to a particular entity and is comprised of a plurality of data fields;
    identifying data fields in the set of records, wherein the data fields contain explicitly identifiable data for an entity;
    obfuscating values in the data fields identified as containing explicitly identifiable data for the entity;
    randomly selecting records in the set of records;
    for each of the selected records, randomly selecting data fields in the selected records;
    removing values in the selected data fields of the selected records in the set of records;
    imputing values in data fields having missing values in the set of records using an imputation method; and
    repeating the steps of removing values and imputing values for a number of iterations and thereby generate a new data set, where the number of iterations exceeds one.

2. The method of claim 1 further comprises obfuscating values in the data fields identified as containing explicitly identifiable data by removing the values from the identified data fields.

3. The method of claim 1 further comprises removing values in randomly selected data fields by randomly selecting data fields in the set of records using an alias method.

4. The method of claim 1 further comprises imputing values in data fields using multivariate imputation by chained equations.

5. The method of claim 1 further comprises, prior to the step of removing values in the data fields, identifying data fields in the set of records having unstructured data format and swapping values of at least one identified data field in a given pair of data records, where the given pair of data records is selected using a similarity measure between the data records in the set of records.

6. The method of claim 5 further comprises pairing a given data record in the set of records with each of the other data records in the set of records;
    computing a similarity measure between values of data fields in each pair of records; and
    identifying the given pair of records from amongst the pair of records, where the given pair of records has the highest similarity measure amongst the pair of records.

7. The method of claim 6 further comprises computing a similarity measures using a Bray-Curtis distance method.

8. The method of claim 5 further comprises
    randomly selecting a given data field in the given data record;
    pairing a given data record in the set of records with each of the other data records in the set of records;
    computing a similarity measure between values of data fields in each pair of records;
    forming a subset of data records from the set of records, where the records in the subset of data records have highest degree of similarity amongst the data records in the set of records;
    randomly selecting a record from the subset of data records; and
    swapping value of the given data field in the given data record with value in the corresponding data field on the randomly selected record from the subset of data records.

9. The method further comprises randomly selecting another data field in the given data record and, for the another data field in the given data record, repeating the steps of claim 8.

10. The method further comprises retrieving another data record in the set of records and, for the another data record, repeating the steps of claim 8.

11. A computer-implemented method for generating a data set from a database, comprising:
    retrieving a set of records from a database, each record pertains to a particular person and is comprised of a plurality of data fields;
    identifying data fields in the set of records, wherein the data fields that contain explicitly identifiable data for a person;
    obfuscating values in the data fields identified as containing explicitly identifiable data for the person;
    selecting at least one data field in a given data record in the set of records;
    selecting a given pair of data records from the set of records, where the given pair of data records is selected using a similarity measure between the data records in the set of records;
    swapping values of the at least one selected data field in the given pair of data records;
    randomly selecting records in the set of records;
    for each of the selected records, randomly selecting data fields in the selected records;
    removing values in the selected data fields of the selected records in the set of records;
    imputing values in data fields having missing values in the set of records using an imputation method; and
    repeating the steps of removing values and imputing values for a number of iterations and thereby generate a new data set, where the number of iterations exceeds one.

12. The method of claim 11 further comprises obfuscating values in the data fields identified as containing explicitly identifiable data by removing the values from the identified data fields.

13. The method of claim 11 further comprises removing values in randomly selected data fields by randomly selecting data fields in the set of records using an alias method.

14. The method of claim 11 further comprises imputing values in data fields using multivariate imputation by chained equations.

15. The method of claim 11 wherein selecting a given pair of data records further comprises pairing the given data record in the set of records with each of the other data records in the set of records;

computing a similarity measure between values of data fields in each pair of records; and identifying the given pair of records from amongst the pair of records, where the given pair of records has the highest similarity measure amongst the pair of records.

16. The method of claim 15 further comprises computing a similarity measures using a Bray-Curtis distance method.

17. The method of claim 11 further comprises randomly selecting a given data field in the given data record;

pairing a given data record in the set of records with each of the other data records in the set of records;

computing a similarity measure between values of data fields in each pair of records;

forming a subset of data records from the set of records, where the records in the subset of data records have highest degree of similarity amongst the data records in the set of records;

randomly selecting a record from the subset of data records; and swapping value of the given data field in the given data record with value in the corresponding data field on the randomly selected record from the subset of data records.

18. The method further comprises randomly selecting another data field in the given data record and, for the another data field in the given data record, repeating the steps of claim 16.

19. The method further comprises retrieving another data record in the set of records and, for the another data record, repeating the steps of claim 16.

* * * * *